United States Patent [19]

Beers et al.

[11] Patent Number: 4,673,750

[45] Date of Patent: Jun. 16, 1987

[54] AUTO-ADHERING ONE-COMPONENT RTV SILICONE SEALANT COMPOSITION UTILIZING GLYCIDOXYALKYL SUBSTITUTED ALKOXY-OXIME SILANE AS AN ADHESION PROMOTER

[75] Inventors: M. Dale Beers, Aurora; James E. Thompson, Lakewood, both of Ohio

[73] Assignee: Loctite Corporation, Newington, Conn.

[21] Appl. No.: 869,452

[22] Filed: Apr. 27, 1986

Related U.S. Application Data

[63] Continuation of Ser. No. 719,753, Apr. 4, 1985, abandoned.

[51] Int. Cl.$^4$ .................... C07D 303/02; C07F 7/10
[52] U.S. Cl. .................................................. 549/215
[58] Field of Search ........................................ 549/215

[56] References Cited

U.S. PATENT DOCUMENTS

| | | | |
|---|---|---|---|
| 2,946,701 | 7/1960 | Plueddemann | 549/215 X |
| 3,035,016 | 5/1962 | Bruner | 556/413 X |
| 3,120,546 | 2/1964 | Plueddemann | 549/215 |
| 3,133,891 | 5/1964 | Ceyzeriat | 556/413 X |
| 3,189,576 | 6/1965 | Sweet | 556/413 X |
| 3,382,205 | 5/1968 | Beers | 556/413 X |
| 3,427,220 | 2/1969 | Northrup | 549/215 X |
| 3,455,877 | 7/1969 | Plueddemann | 549/215 X |
| 3,485,780 | 12/1969 | Sterman et al. | 549/215 X |
| 3,517,001 | 6/1970 | Berger | 556/413 X |
| 3,541,044 | 11/1970 | Beers et al. | 556/413 X |
| 3,687,606 | 8/1972 | Simmler et al. | 549/215 X |
| 3,691,206 | 9/1972 | Northrup | 549/215 |
| 3,702,783 | 11/1972 | Hartlein | 549/215 X |
| 3,776,933 | 12/1973 | Toporcer | 556/413 X |
| 3,837,878 | 9/1974 | Beers | 556/413 X |
| 3,847,848 | 11/1974 | Beers | 556/413 X |
| 3,962,160 | 6/1976 | Beers et al. | 556/413 X |
| 3,998,991 | 12/1976 | Kaas | 549/215 X |
| 4,069,368 | 1/1978 | Deyak et al. | 549/215 X |
| 4,100,129 | 7/1978 | Beers | 556/413 X |
| 4,213,908 | 7/1980 | Kotzsch et al. | 549/215 |
| 4,323,489 | 4/1982 | Beers | 556/413 UX |
| 4,356,116 | 10/1982 | Beers | 556/413 UX |
| 4,395,526 | 7/1983 | White et al. | 556/413 UX |

Primary Examiner—Paul F. Shaver
Attorney, Agent, or Firm—Eugene F. Miller; Daniel J. Hudak

[57] ABSTRACT

An auto-adhering one-component room temperature vulcanizable silicone sealant utilizes a gylcidoxyalkyl substituted mixed alkoxy-oxime silane as an adhesion promoter. The sealant bonds to a variety of substrates including glass, metal, ceramics; does not require a primer to be applied to the substrate; has a low odor and is non-corrosive to ferrous substrates. The sealant is useful as a formed-in-place gasket material as for example, an internal combustion engine and has good oil resistance for an RTV silicone gasketing material.

7 Claims, No Drawings

1

AUTO-ADHERING ONE-COMPONENT RTV SILICONE SEALANT COMPOSITION UTILIZING GLYCIDOXYALKYL SUBSTITUTED ALKOXY-OXIME SILANE AS AN ADHESION PROMOTER

This application is a continuation of Ser. No. 719,753 filed Apr. 4, 1985, now abandoned.

TECHNICAL FIELD

The present invention relates to a glycidoxy alkyl substituted alkoxy-oxime silane as an adhesion promoter, which can be used in a silicone sealant.

BACKGROUND ART

Heretofore, various silicone adhesive sealants applied to an iron containing substrate had a disadvantage of initially being corrosive. These same sealants also required a silicone resin primer to be initially applied to the substrate before they could be coated thereon. They also tended to have a disagreeable odor and generally did not have good oil resistance, especially at elevated temperatures.

U.S. Pat. No. 3,189,576 to Sweet relates to oxime curatives and to new organosilicone intermediates.

U.S. Pat. No. 4,323,489 as well as U.S. Pat. No. 3,962,160, both to Beers, generally relate to oxime cureable room temperature vulcanizates. More specifically, the U.S. Pat. No. 4,323,489 relates to a vulcanizable silicone rubber composition with very low modulus containing a silanol end-stopped diorganopolysiloxane, a difunctional acetamide coupler as a chain extender and a minor amount of a compound containing an oxime functionality thereon as a trifunctional crosslinker.

U.S. Pat. No. 4,356,116 to Beers relates to a low volatile room temperature vulcanizable silicone rubber composition containing various components including a silanol polymer, a crosslinking agent, and a filler.

U.S. Pat. No. 3,517,001 to Berger relates to adhesion promoter compositions.

U.S. Pat. No. 4,100,129 to Beers also relates to adhesion promoter compositions curable in the presence of moisture.

U.S. Pat. No. 4,395,526 to White et al relates to a stable, substantially acid-free, one-component curable polyalkoxy-terminated organosiloxane composition having a condensation catalyst, such as a tin compound. The material in this patent also serves as an adhesion promoter.

Specific patents relating to acetoxy curing room temperature vulcanizable silicones include Ceyzeriat, U.S. Pat. No. 3,133,891, Brunner, No. 3,035,016, and Beers, No. 3,382,205. More specifically, the Beers' patent relates to organopolysiloxane composition comprising a mixture of organotriacyloxysilane and a base mixture containing organosiloxane having chemically combined organosiloxy units.

U.S. Pat. No. 3,541,044 to Beers relates to a substantially anhydrous organopolysiloxane composition curable to the elastomeric state upon exposure to moisture. Another patent by Beers, namely U.S. Pat. No. 3,837,878 relates to a two-component room temperature vulcanizable silicone rubber composition suitable for molding applications whereas U.S. Pat. No. 3,837,878 also to Beers relates to a process for treating silicone fillers.

U.S. Pat. No. 3,776,933 to Toporcerer relates to chain extenders with regard to RTV systems.

The above patents do not teach or suggest an adhesion promoter composition or compound containing a glycidoxyalkyl substituted mixed alkoxy-oxime silane or such a silane which has low odor, is non-corrosive to iron substrates, and has good adhesion as well as good oil resistance.

DISCLOSURE OF INVENTION

It is therefore an aspect of the present invention to provide an adhesion promoter comprising a glycidoxyalkyl substituted mixed alkoxy-oxime silane-type compound.

It is a yet further aspect of the present invention to provide an adhesion promoter, as above, which is utilized in an auto-adhering one-component RTV silicone sealant; and which sealant composition is non-corrosive to ferrous and aluminum substrates, has a low odor and eliminates the need for a primer coat to obtain good adhesion.

It is another aspect of the present invention to provide an auto-adhering one-component RTV silicone sealant, as above, which has good oil resistance.

It is another aspect of the present invention to provide an auto-adhering one-component RTV silicone sealant, as above, which has good oil resistance.

It is yet a further aspect of the present invention to provide an auto-adhering one-component RTV silicone sealant, as above, which has good adhesion to substrates such as steel, iron, aluminum, acrylic plastics and paints, polycarbonate, polyester, ABS, glass, ceramics, brick, concrete and the like.

These and other aspects of the present invention will become apparent from the following specification.

The inventive adhesion promoter is a compound having the formula:

$$(R^7)_2-C\overset{O}{\underset{}{\diagup\diagdown}}CH-R^1-O-R^2-\underset{(R^6)_p}{\overset{|}{Si}}-(OR^3)_m \left( \underset{N=C}{\overset{O}{\diagdown\diagup}} \overset{R^4}{\underset{R^5}{\diagup\diagdown}} \right)_x$$

wherein $R^1$ is a hydrocarbyl, or a halohydrocarbyl having from 1 to 10 carbon atoms; $R^2$ is a divalent hydrocarbyl, or a halohydrocarbyl having from 1 to 10 carbon atoms; $R^3$ is a hydrocarbyl, a halohydrocarbyl, or a carboxyalkyl having from 1 to 10 carbon atoms; m is from 0 to 3, $R^4$ and $R^5$ can independently be a hydrocarbyl, halohydrocarbyl or carboxyalkyl having from 1 to 10 carbon atoms; x is 0 to 3; $R^6$ is hydrocarbyl, a halohydrocarbyl, or a carboxyalkyl having from 1 to 10 carbon atoms; p is 0-2; and the $R^7$ groups are independently hydrogen, hydrocarbyl, halohydrocarbyl, or carboxyalkyl having from 1 to 10 carbon atoms; and $x+m+p=3$.

The adhesion promoter of the present invention can be utilized in silicone sealants. When so utilized, the sealant sealant composition exhibits very good auto-adhering adhesion even on oil contaminated metal such as aluminum and steel surfaces as encountered in the auto industry. Additionally, such compositions have excellent oil resistance properties, even at high temperatures for example, 300° F., and are particularly useful as silicone formed-in-place gasketing.

According to the concepts of the present invention an auto adhering one-component RTV silicone sealant is prepared utilizing a glycidoxyalkyl adhesion substituted mixed alkoxy-oxime silane. The adhesion promoter can be presented by the following formula.

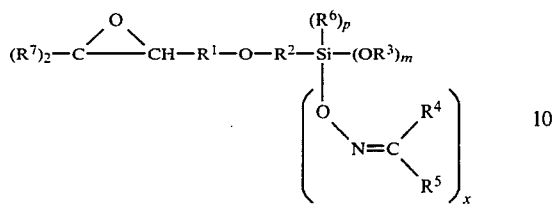

$R^1$ is a hydrocarbyl having from 1 to 10 carbon atoms. Throughout this entire specification, by the term "hydrocarbyl" it is meant that the hydrocarbon group is an aliphatic or cycloaliphatic group such as an alkyl, an alkenyl, an acetylene group or cycloalkyl, etc. with alkyl being preferred, or an aromatic group including aliphatic substituted aromatic or an aromatic substituted aliphatic. This definition of hydrocarbyl is applicable not only with regard to $R^1$ but also with regard to $R^2$ through $R^8$ groups with the exception that $R^3$ does not contain aromatic groups. $R^1$ can also be a halohydrocarbyl having from 1 to 10 carbon atoms. Generally, an alkylene group is desired with methylene being preferred.

$R^2$ can be a hydrocarbyl group, or a halohydrocarbyl having from 1 to 10 carbon atoms. A 3-6 carbon alkylene group is desired, preferably a 3 carbon alkylene group.

The $R^3$ group can be a hydrocarbyl group, a halohydrocarbyl group or a carboxyalkyl group having from 1 to 10 carbon atoms. Desirably, an alkyl group is preferred with methyl being highly preferred. The number of "$OR^3$" groups or "m" is from 0 to 3, desirably 1 to 2 with 1 being preferred. With regard to the substituents on the oxime group, $R^4$ and $R^5$ can be the same or different and include a hydrocarbyl, a halohydrocarbyl, or a carboxyalkyl, all having from 1 to 10 carbon atoms. Generally, alkyl groups are desired with methyl or ethyl being highly preferred. The number of oxime groups on the silicon atom, that is "x" is generally from 0 to 3, desirably 1 to 3, with 2 being preferred. $R^6$ is a hydrocarbyl, a halohydrocarbyl, or a carboxyalkyl having from 1 to 10 carbon atoms. The number of such $R^6$ groups, that is "p" can be 0 to 2, preferably 0. $R^7$ can be hydrogen, hydrocarbyl, halohydrocarbyl, or carboxyalkyl having from 1 to 10 carbon atoms with methyl being desirable. Preferrably, however, both $R^7$ groups are H.

Examples of specific adhesion promoters according to the present invention include the following compounds:

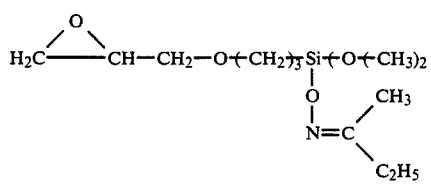

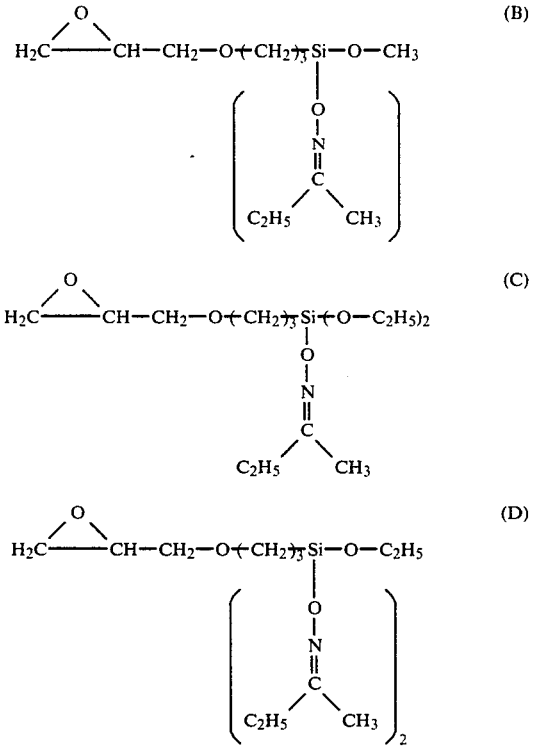

The adhesion promoter of the present invention having the above formulation is prepared in the manner as set forth below involving reaction of a glycidoxy silane compound with an oxime compound.

The overall reaction of a glycidoxyalkyl silane compound with an oxime compound can be represented as follows:

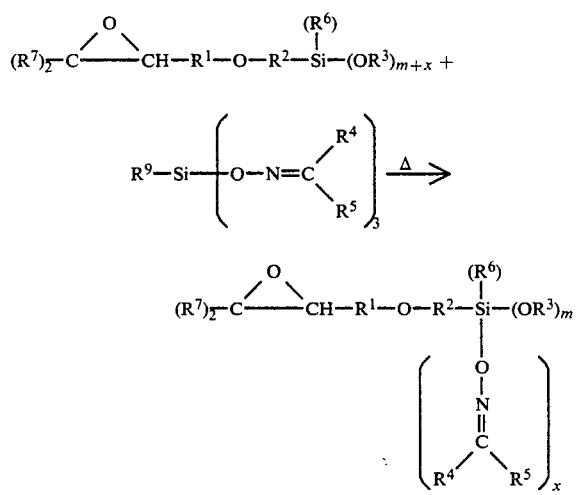

The oxime crosslinking units are grafted onto the glycidoxyalkyl silane by carrying out the reaction at a temperature from about 45° C. to about 150° C., preferably from about 50° C. to about 120° C. An inert gas blanket for example nitrogen, is utilized to avoid reaction with moisture. The type of oxime compounds utilized are generally of the type set forth in formulae A and B below or mixtures thereof. As should be apparent from the reaction set forth above, a large variety of different compounds can be made according to the present invention.

In carrying out the reaction of forming the adhesion promoter, an organic tin salt catalyst is generally utilized. The amount of tin catalyst is generally from about 0.01 to aboout 0.5 percent by weight and preferably from about 0.02 to about 0.2 by weight based upon the total amount of said silicone sealant compound. Such tin catalysts are generally well known to the art, such as those set forth in U.S. Pat. Nos. 4,356,116 and 4,395,526 hereby fully incorporated by reference. Examples of specific tin catalysts include dibutyltindilaurate, dibutyltindiacetate, tin octoate, dimethyltindibutyrate, triethyltintartrate, tin oleate, dibutyltinoxide and dimethyltin bisneodecanoate.

The adhesion promoter as discussed above forms a part of a silicone composition containing various components thereof such as a base polymer, a plasticizer, a thixotropic agent, and the like. Considering the base polymer, it is a silanol terminated diorganopolysiloxane polymer. This linear polymer may be devolatilized in a manner such as set forth in U.S. Pat. No. 4,356,116 and generally has a viscosity of from about 2,000 to about 250,000 centipoise and preferably from about 10,000 to about 120,000 centipoise. The polymer has the formula

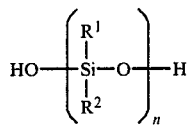

where n is from about 300 to about 1,000, where $R^1$ and $R^2$ can be the same or different, where $R^1$ and $R^2$ is an alkyl group having from 1 to 8 carbon atoms with methyl being preferred, a cycloalkyl group having from 4 to 7 carbon atoms such as cyclohexyl, an alkenyl group having from 2 to 8 carbon atoms such as allyl with vinyl being preferred, an aryl or an alkyl substituted aryl group having from 6 to 14 carbon atoms such as phenyl, methylphenyl, or a fluoroalkyl group having from 1 to 8 carbon atoms with 3,3,3-trifluoropropyl being preferred. The amount of the linear polymer generally ranges from about 25 to about 90 percent by weight and preferably from 30 to about 60 percent by weight based upon the total weight of the low modulus RTV silicone composition. Such polymers are commercially available and are manufactured by Mobay, Union Carbide and Wacker Chemie.

Generally, the silanol terminated silicone polymer also is reacted with an oxime compound having the formulation set forth in formula A wherein the oxime compound is grafted onto the polymer. Simple types of oxime compounds which can be utilized in the present invention are set forth in formulations A and/or B wherein on a molar basis, from 0.0 or 0.05 moles to about 0.4 moles of the formula A oxime is utilized and preferably from about 0.1 to about 0.2 moles of the formulation A oxime compound per 1 mole of said Formula "A" and "B" compounds. Naturally, the amount of the Formula "B" compound is the difference, that is from 0.6 to 0.95 and preferably from 0.8 to 0.9 moles per 1 mole of said Formula "A" and said "B" compounds.

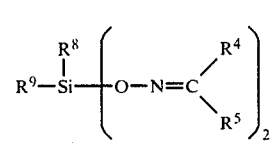

Formula "A"

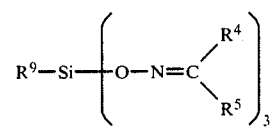

Formula "B"

$R^4$ and $R^5$ are as set forth above. $R^9$ can be an alkyl having from 1 to 8 carbon atoms with methyl being preferred, an alkenyl group having from 2 to 8 carbon atoms with vinyl being preferred, a haloalkyl having from 1 to 8 carbon atoms, a trifluoroalkyl having from 1 to 8 carbon atoms, or a haloalkenyl having from 2 to 8 carbon atoms. $R^8$ can be a hydrocarbyl, a halohydrocarbyl, or a carboxyalkyl having from 1 to 10 carbon atoms. Preferably $R^8$ is methyl or ethyl.

Generally, when an oxime compound is utilized as set forth in Formula A wherein $R^4$ is methyl, $R^5$ is ethyl, $R^9$ is methyl or vinyl and $R^8$ is methoxy, an unexpected synergistic result is obtained with regard to adhesion. An enhancement of adhesion results. The enhancement is maximized when $R^9$ is vinyl.

Once the adhesion promoter has been formed, the amount thereof generally utilized in the overall silicone sealant composition is from about 0.5 percent to about 3 percent by weight with from about 0.8 percent to about 2 percent by weight being preferred.

Preparation of an oxime type compound as set forth in Formula A is generally well known to the art and literature, as for example U.S. Pat. No. 3,189,576 which is hereby fully incorporated by reference as to the manner and method of preparing such oxime compounds. In order to insure that gellation or viscosity increases do not occur, an excess of the crosslinker containing the oxime group to the silanol in the base polymer, set forth below, is utilized at a ratio of from about 1.2 to about 4.0 with from about 2.0 to about 3.0 being preferred molar ratio of crosslinker to silanol groups.

The plasticizer utilized along with the linear base polymer in the sealant composition is a devolatilized triorganosiloxy terminated diorganopolysiloxane fluid existing in an amount of from 0 to 1 to about 40 percent by weight and desirably from 5 to about 25 percent by weight based upon the total weight of the siloxane sealant composition. The plasticizer lowers the durometer and modulus of the cured rubber and lowers the viscosity of the overall system or composition. However, the viscosity of the plasticizer should not be too low inasmuch as it will tend to bleed out of the composition. Accordingly, the viscosity generally ranges from about 50 to about 100,000 centipoise and preferably from about 500 to about 10,000 centipoise.

The plasticizer is a diorganopolysiloxane polymer terminated with monofunctional, triorgano siloxy end groups. The organo compounds within the repeating units are the same as $R^1$ and $R^2$ set forth herein above with regard to the base polymer. However, it may contain trace quantities of trifunctional monoorganosiloxy units originating from impurities in the starting materials. The siloxy units contain an alkyl group having from 1 to 8 carbon atoms with methyl being preferred. The number of repeating units in the plasticizer is generally from about 20 to about 900. As with the linear base polymer, the plasticizer is devolatilized in accordance with any conventional manner or process, well known to the art. A specific example of devolatilization is seth forth in U.S. Pat. No. 34,356,116 which is hereby fully incorporated by reference.

In order to reinforce the polymer network as well as to impart non-sag properties to the system, a thixotropic agent is added to the overall composition. This agent which also adds physical strength to the system desirably is a treated or an untreated silica filler with a treated fumed silica filler being preferred. Treated or untreated silica fillers are well known to the art and generally any such conventional filler can be utilized. Examples of specific silica fillers are set forth in U.S. Pat. No. 3,837,878 whuich is hereby full incorporated by reference. Additionally, treated silica as set forth in Lucas U,.S. Pat. No. 2,938,009, Lichtenwalner U.S. Pat. No. 3,004,859, and Smith U.S. Pat. No. 3,635,743, all hereby full incorporated by reference, can be utilized. Typically, the silica filler has a very high surface area such as about 200M$^2$/gram.

Optionally, from about 0.1 to about 5 percent by weight and preferably from about 0.2 to about 3 percent by weight based upon the total weight of the overall system or composition composition of a thermal aging additive can be utilized. This optional component functions to reduce oxidation and thermal rearrangement of polymers at elevated temperatures. These antioxidants may include materials like cerium neodecanoate, rare earth octoates and iron octoates. Representative samples can also usually include thermal aging additives such as carbon black, iron oxide powder, and titanium dioxide. Naturally, other pigments can be utilized.

Another optional ingredient is an inert non-reinforcing filler such as ground quartz, calcium carbonate, talc, clay, various silicate compounds and other materials well known in the art. The amount utilized is from about 5% to about 60% by weight bases upon the total weight of the sealant composition.

The sealants of the present invention containing the adhesion promoter therein exhibits numerous improved and desirous properties. For example, a silicone resin primer is no longer needed to obtain good adhesion, but rather a silicone sealant of the present invention can be directly applied to a metallic or other surface. For example, the sealant composition of the present invention has good adhesion to various substrates such as steel, iron, aluminum, acrylic plastics and paints, polycarbonate, polyester, ABS, glass, ceramics, brick, concrete and the like. Moreover, the silicone sealants of the present invention have low odor characteristics as opposed to the sometime nauseating odor of prior art sealants and are generally non-corrosive with regard to iron or aluminum substrates.

The silicon sealants of the present invention can be utilized as in-place gasketing sealants due to their good thermal resistance at high temperatures as for example from about 250° F. to about 500° F. and still maintain good flexibility at low temperatures, that is about 85° F. Particular uses include RTV silicone adhesives, bathtub caulking compounds, masonry joint materials, as a plastic adhesive, and the like. The silicone sealants are particularly suitable for usage in various internal combustion engine for various gasket applications such as oil pan gaskets, valve cover gaskets, water seals, intake seals, and the like.

The preparation and incorporation of the aforementioned silane adhesion promoter can be accomplished according to one of two modes. In the first mode, there is a reaction product of various oxime type products and thus the exact end product or type is not known. In the second mode, a specific oxime product is produced.

In the first mode of preparation from about 0.5 to 4 parts of a glycidoxyalkyl trialkoxysilane is added to the crosslinker mixture consisting of about 12 parts of the oxime curing agent set forth above and this mixture is heated at 50° C. for about 20 hours in a closed container or about 4 hours at 120° C. in a sealed container.

The silicone sealant compound is then prepared by charging the various ingredients into a mixer under dry conditions as through the use of dry nitrogen to prevent hydrolysis of the oxime crosslinking compound. Generally, the polymer is added first with the plasticizer. The oxime crosslinker and adhesion promoter composition is then added followed by the fumed silica, as well as any thermal stabilizing agent. The treated calcium carbonate filter is then added. The composition is mixed under high speed or agitation as well as under a vacuum for several minutes or even hours to remove the entrapped nitrogen bubbles. The resulting paste formed can be placed or extruded into a desirable container and the like.

The invention will be better understood by reference to the following example:

EXAMPLE 1

|  | Weight % |
|---|---|
| 1. 10,000 cps. viscosity silanol terminated polydimethylsiloxane | 40.06 |
| 2. 1000 cps trimethylsilyl terminated polydimethylsiloxane | 15.46 |
| 3. Stearic acid treated calcium carbonate | 34.05 |
| 4. Polydimethylsiloxane treated fumed silica having a surface area of approximately 200 m$^2$/gram | 3.61 |
| 5. Iron oxide | 1.40 |
| 6. Methyltris-methylethylketoximosilane | 4.81 |
| 7. Dimethyltinbisneodecanoate | 0.08 |
| 8. Gamma-glycidoxypropyltrimethoxysilane | 0.53 |

This composition was prepared by charging the ingredients into the mixing can of a vertical laboratory change can mixer which had been flushed with dry nitrogen to prevent the hydrolysis of the oxime crosslinker.

Ingredients (6), (7) and (8) were heated in a closed glass jar in a 50° C. oven for 16 hours and allowed to cool before incorporation into the sealant formulation. The ingredients were subsequently added as follows: (1), (2), (3), (4), and (5), then the mixture of (6), (7) and (8) and mixed at high speed under vacuum for approximately two hours and afterwards the resulting paste was transferred to a pressure Semco mixer. It was then extruded from the pressure Semco into six ounce polyethylene cartridges.

It was found that the 180° F. peel adhesion of this sealant to Alclad aluminum after curing for 14 days was 8 to 10 pounds per linear inch with 100% cohesive failure versus 0 to 2 pounds per linear inch with 100% adhesive failure for a sealant without (8) and also for a sealant with (8) but excluding in the preparation of said sealant the step of heating at 50° C. for 16 hours the mixture of (6), (7) and (8).

In the second mode of preparation a glycidoxyalkyl trialkoxysilane is heated with a sufficient amount of a ketoxime compounds such as methyl ethylketoxime to cause a partial substitution of the ketoxime on the silicon atom by displacing the alkoxy moiety. The sealant is prepared as described for the first mode of preparation.

This mode of preparation can be better understood by reference to the following examples.

EXAMPLE 2

47.28 g (0.2 mole) of gamma-glycidoxypropyltrimethoxy silane and 19.18 (0.22 mole of methyl ethyl ketoxime were charged to a glass flask and heated under nitrogen at 120° C. for 16 hours. The resulting analysis by gas chromatograph indicated partial substitution of the methoxy moieties by methyl ethyl ketoximo moieties on the silicon atom. Mono, di, and trisubstituted species were indicated.

EXAMPLE 3

| | Weight % |
|---|---|
| 1. 10,000 cps. viscosity silanol terminated polydimethylsiloxane | 40.06 |
| 2. 1000 cps trimethylsilyl terminated polydimethylsiloxane | 15.46 |
| 3. Stearic acid treated calcium carbonate | 34.05 |
| 4. Polydimethylsiloxane treated fumed silica having a surface area of approximately 200 m²/gram | 3.61 |
| 5. Iron oxide | 1.40 |
| 6. Methyltris-methylethylketoximosilane | 4.81 |
| 7. Dimethyltinbisneodecanoate | 0.08 |
| 8. The material of Example 2 | 0.53 |

This composition was prepared as in Example 1. The ingredients were added in the order: (1), (2), (3), (4), (5), (6), (7), and (8), then mixed at high speed under vacuum for approximately two hours and afterward the resulting paste was transferred to a pressure Semco mixer and extruded into six ounce polyethylene cartridges. The peel adhesion of this sealant to Alclad aluminum after curing for four weeks was 13 pli (lbs. per linear inch) with 100% cohesive failure.

While in accordance with the patent statutes, a best mode and preferred embodiment have been described in detail, the scope of the invention is not limited thereto, but rather by the scope of the attached claims.

What is claimed is:

1. An adhesion promoter, comprising: A compound having the formula:

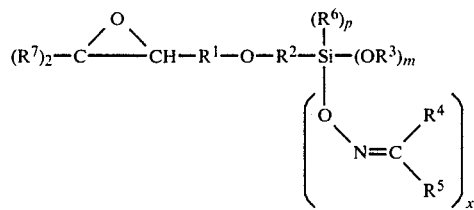

wherein $R^1$ is hydrocarbyl, or halohydrocarbyl having from 1 to 10 carbon atoms; $R^2$ is a divalent hydrocarbyl, or a halohydrocarbyl having from 1 to 10 carbon atoms; $R^3$ is a hydrocarbyl, a halohydrocarbyl, or a carboxyalkyl having from 1 to 10 carbon atoms; m is from 0 to 2, $R^4$ and $R^5$ is independently a hydrocarbyl, halohydrocarbyl or carboxyalkyl having from 1 to 10 carbon atoms; x is 1 to 3; $R^6$ is hydrocarbyl, a halohydrocarbyl, or a carboxyalkyl having from 1 to 10 carbon atoms; p is 0-2; and the $R^7$ groups are independently hydrogen, hydrocarbyl, halohydrocarbyl, or carboxyalkyl having from 1 to 10 carbon atoms; and $x+m+p=3$.

2. An adhesion promoter according to claim 1, wherein $R^1$ and $R^2$ are alkylene groups, $R^3$, $R^4$ and $R^5$ are the same or different alkyl groups, the $R^7$ groups are both hydrogen and p is 0.

3. An adhesion promoter according to claim 2 wherein $R^1$ is methylene, $R^2$ is propylene, m is at least one and $R^3$ is methyl or ethyl.

4. An adhesion promoter according to claim 1, wherein $R^4$ and $R^5$ are selected from the group consisting of methyl or ethyl.

5. An adhesion promoter according to claim 4, wherein $R^4$ is methyl and $R^5$ is ethyl.

6. An adhesion promoter comprising the reaction product of one or more compounds having the formula:

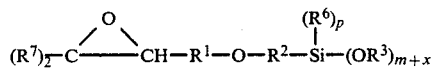

where $R^1$ is hydrocarbyl, or halohydrocarbyl having 1-10 carbon atoms, $R^2$ is hydrocarbyl or halohydrocarbyl having 1-10 carbon atoms; $R^3$ is hydrocarbyl, halohydrocarbyl or carboxyalkyl having 1-10 carbon atoms; $R^6$ is hydrocarbyl, halohydrocarbyl or carboxyalkyl having 1-10 carbon atoms; m is 1-3; the $R^7$ groups are independently hydrogen, hydrocarbyl, halohydrocarbyl, or carboxyalkyl having from 1 to 10 carbon atoms; p is 0-2 and $m+p=3$, with one or more compounds having the formulae A or B:

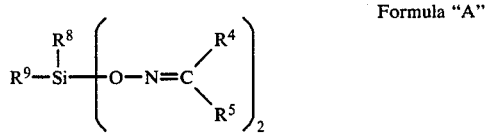

Formula "A"

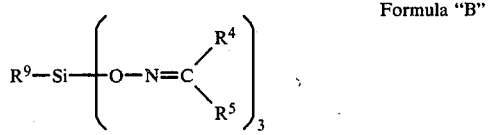

Formula "B"

or mixtures thereof, where $R^4$, $R^5$ and $R^8$ are as defined for $R^3$, and $R^9$ is alkyl having 1-8 carbon atoms, trifluoroalkyl having 1-8 carbon atoms, or haloalkenyl having 2-8 carbon atoms.

7. An adhesion promoter as in claim 6 wherein the said reaction is carried out at a temperature of between 45° C. and 150° C.

* * * * *

UNITED STATES PATENT OFFICE
CERTIFICATE OF CORRECTION

Patent No. 4,673,750           Dated   June 16, 1987

Inventor(s)                Beers et al.

It is certified that error appears in the above-identified patent and that said Letters Patent are hereby corrected as shown below:

On the cover page, delete the filing date of "April 27, 1987" and insert the actual filing date of --May 27, 1986--.

Signed and Sealed this

Twenty-ninth Day of November, 1988

*Attest:*

DONALD J. QUIGG

*Attesting Officer*    Commissioner of Patents and Trademarks